United States Patent [19]

Biggadike et al.

[11] Patent Number: 6,114,318
[45] Date of Patent: Sep. 5, 2000

[54] 17β-(2-OXO-TETRAHYDROFURANYL)-THIO-SUBSTITUTED ANDROSTANE DERIVATIVES

[75] Inventors: Keith Biggadike; Panayiotis Alexandrou Procopiou, both of Stevenage, United Kingdom

[73] Assignee: Glaxo Group Limited, Greenford, United Kingdom

[21] Appl. No.: 09/091,747

[22] PCT Filed: Dec. 19, 1996

[86] PCT No.: PCT/GB96/03138

§ 371 Date: Jun. 24, 1998

§ 102(e) Date: Jun. 24, 1998

[87] PCT Pub. No.: WO97/24368

PCT Pub. Date: Jul. 10, 1997

[30] Foreign Application Priority Data

Dec. 29, 1995 [GB] United Kingdom .................... 9526677
Jun. 21, 1996 [GB] United Kingdom .................... 9613120

[51] Int. Cl.[7] .......................... C07J 71/00; A61K 31/565
[52] U.S. Cl. ................. 514/174; 540/65; 540/67
[58] Field of Search ........................ 540/65, 67; 514/174

[56] References Cited

U.S. PATENT DOCUMENTS 4,481,144  11/1984  Varma ................................ 260/397.45

FOREIGN PATENT DOCUMENTS 0 161 187  11/1985  European Pat. Off. .
WO 94/14834  7/1994  WIPO .

*Primary Examiner*—Mukund J. Shah
*Assistant Examiner*—Brenda Coleman
*Attorney, Agent, or Firm*—Nixon & Vanderhye

[57] ABSTRACT

Compounds of the androstane series are described having the formula (I)

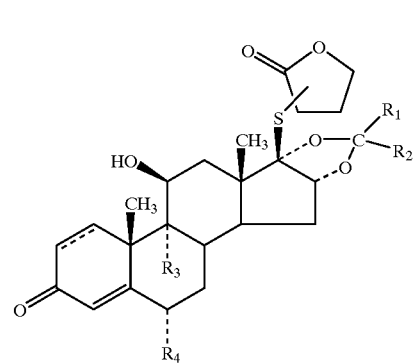

(I)

and solvates thereof in which $R_1$ and $R_2$ are the same or different and each represents hydrogen or $C_{1-6}$ alkyl; $R_3$ and $R_4$ are the same or different and each represents hydrogen or halogen; and

----- represents a single or a double bond. Compounds of formula (I) and their solvates are useful as anti-inflammatory or anti-allergic agents.

13 Claims, No Drawings

17β-(2-OXO-TETRAHYDROFURANYL)-THIO-SUBSTITUTED ANDROSTANE DERIVATIVES

This application is a national stage entry under 35 U.S.C. §371 of PCT/GB96/03138, filed Dec. 19, 1996.

The present invention relates to novel anti-inflammatory and anti-allergic compounds of the androstane series and to processes for their preparation. The present invention also relates to pharmaceutical formulations containing the compounds and to therapeutic uses thereof, particularly for the treatment of inflammatory and allergic conditions.

Glucocorticosteroids which have-anti-inflammatory properties are known and are widely used for the treatment of inflammatory disorders or diseases such as asthma and rhinitis. However, such glucocorticosteroids may suffer from the disadvantage of causing unwanted systemic effects following administration. WO94/13690, WO94/14834, WO92/13873 and WO92/13872 all disclose glucocorticosteroides which are alleged to possess anti-inflammatory activity coupled with reduced systemic potency.

The present invention provides a novel group of compounds which possess useful anti-inflammatory activity whilst having little or no systemic activity. Thus, the compounds of the present invention represent a safer alternative to those known glucocorticoids which have poor side-effect profiles.

Thus, according to one aspect of the invention, there is provided a compound of formula (I)

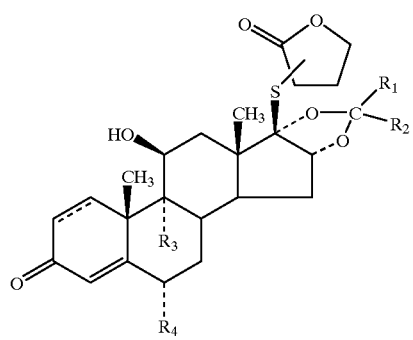

(I)

and solvates thereof in which $R_1$ and $R_2$ are the same or different and each represents hydrogen or $C_{1-6}$ alkyl;

$R_3$ and $R_4$ are the same or different and each represents hydrogen or halogen; and

----- represents a single or a double bond.

In the above definitions, the term "alkyl" as a group or part of a group means a straight chain or, where available, a branched chain alkyl moiety. For example, it may represent a $C_{1-4}$ alkyl function as represented by methyl, ethyl, n-propyl, i-propyl, n-butyl, s-butyl and t-butyl.

The solvates may, for example, be hydrates.

References hereinafter to a compound according to the invention includes both compounds of formula (I) and their solvates, particularly pharmaceutically acceptable solvates.

It will be appreciated that the invention includes within its scope all stereoisomers of the compounds of formula (I) and mixtures thereof.

In particular the compounds of formula (I) contain an asymmetric centre at the point of attachment of the lactone moiety. Thus, the invention includes within its scope both diastereoisomers at this asymmetric centre and mixtures thereof.

Diastereoisomers and mixtures thereof at the asymmetric centre

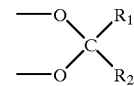

when $R_1$ and $R_2$ are different are also included within the scope of the present invention.

The sulphur linkage may be to the alpha, beta or gamma carbon atoms of the lactone group,

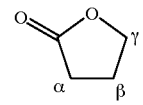

however, compounds of formula (I) in which S is bonded to the alpha atom are generally preferred.

A preferred group of compounds are compounds of formula (I) in which $R_1$ and $R_2$ which may be the same or different each represents hydrogen or $C_{1-3}$ alkyl, particularly hydrogen, methyl or n-propyl.

Compounds of formula (I) in which $R_3$ and $R_4$, which can be the same or different, each represents hydrogen, fluorine or chlorine, particularly hydrogen or fluorine, are preferred. Especially preferred are compounds in which both $R_3$ and $R_4$ are fluorine.

A particularly preferred group of compounds of the invention are compounds of formula (I) in which $R_1$ and $R_2$ are the same or different and each represents hydrogen or $C_{1-3}$ alkyl, especially hydrogen, methyl or n-propyl; $R_3$ and $R_4$ which can be the same or different each represents hydrogen or fluorine, especially fluorine; and

----- represents a single or a double bond. The R-isomers of compounds within this group in which $R_1$ and $R_2$ are different are particularly preferred.

It is to be understood that the present invention covers all combinations of particularly and preferred groups referred to hereinabove.

Compounds of formula (I) include:

6α,9α-Difluoro-11β-hydroxy-16α,17α-isopropylidenedioxy-17β-(2-oxo-tetrahydro-furan-3-yl-sulfanyl)-androst-4-en-3-one;

6α,9α-Difluoro-11β-hydroxy-16α,17α-isopropylidenedioxy-17β-(2-oxo-tetrahydro-furan-3-yl-sulfanyl)-androsta-1,4-dien-3-one;

16α,17α-(R-Butylidenedioxy)-6α,9α-difluoro-11β-hydroxy-17β-(2-oxo-tetrahydro-furan-3-yl-sulfanyl)-androsta-1,4-dien-3-one;

16α,17α-(R-Butylidenedioxy)-6α,9α-difluoro-11β-hydroxy-17β-(2-oxo-tetrahydro-furan-4-yl-sulfanyl)-androst-4-en-3-one;

16α,17α-(R-Butylidenedioxy)-6α,9α-difluoro-11β-hydroxy-17β-(2-oxo-tetrahydro-furan-3-yl-sulfanyl)-androst-4-en-3-one;

and solvates thereof.

It will be appreciated that each of the above compounds of formula (I) includes the individual R and S diastereoisomers at the asymmetric centre at the point of attachment of the lactone moiety as well as mixtures thereof. It will further be appreciated that the compounds of formula (I) may include the individual diastereoisomers at the asymmetric centre

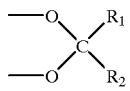

when $R_1$ and $R_2$ are different.

Thus, the individual R and S diastereoisomers isolated such as to be substantially free of the other diastereoisomer ie pure and mixtures thereof are included within the scope of the present invention. An individual R or S diastereoisomer such as to be substantially free of the other diastereoisomer ie pure will be isolated such that less than 10%, preferably less than 1% e.g. less than 0.1% of the other diastereoisomer is present.

The compounds of formula (I) have potentially beneficial anti-inflammatory or anti-allergic effects, particularly upon local administration, demonstrated by, for example, their ability to bind to the glucocorticoid receptor and to illicit a response via that receptor. Hence, the compounds of formula (I) are useful in the treatment of inflammatory and/or allergic disorders. Further, compounds of formula (I) possess the advantage of having little or no systemic activity. Therefore, the compounds of the invention may represent a safer alternative to those known anti-inflammatory glucocorticoids which have poor side effect profiles.

Examples of disease states in which the compounds of the invention have utility include skin diseases such as eczema, psoriasis, allergic dermatitis neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

Compounds of the invention may also have use in the treatment of conjunctiva and conjunctivitis.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory and anti-allergic agents.

There is thus provided as a further aspect of the invention a compound of formula (I) or a physiologically acceptable solvate thereof for use in human or veterinary medicine, particularly in the treatment of patients with inflammatory and/or allergic conditions.

According to another aspect of the invention, there is provided the use of a compound of formula (I) or physiologically acceptable solvate thereof for the manufacture of a medicament for the treatment of patients with inflammatory and/or allergic conditions.

In a further or alternative aspect, there is provided a method for the treatment of a human or animal subject with an inflammatory and/or allergic condition, which method comprises administering to said human or animal subject an effective amount of a compound of formula (I) or physiologically acceptable solvate thereof.

The compounds according to the invention may be formulated for administration in any convenient way, and the invention therefore also includes within its scope pharmaceutical compositions comprising a compound of formula (I) or physiologically acceptable solvate thereof together, if desirable, in admixture with one or more physiologically acceptable diluents or carriers.

The compounds according to the invention may, for example, be formulated for oral, buccal, sublingual, parenteral, local or rectal administration, especially local administration.

Local administration as used herein, includes administration by insufflation and inhalation. Examples of various types of preparation for local administration include ointment, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers), or as liposome or microencapsulation preparations.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol.

Advantageously, the formulations of the invention may be buffered by the addition of suitable buffering agents.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain between 20 μg–10 mg of the compound of formula (I). Alternatively, the compounds of the invention may be presented without excipients such as lactose.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1.0% and preferably 0.01 to 0.5%. However, in powders for inhalation or insufflation the proportion used will be within the range of from 0.1–2%.

Aerosol formulations are preferably arranged so that each metered dose or "puff" of aerosol contains 20 μg–2000 μg, preferably about 20 μg–500 μg of a compound of formula (I). Administration may be once daily or several times daily, for example 2, 3, 4 or 8 times, giving for example 1, 2 or 3 doses each time. The overall daily dose with an aerosol will be within the range 100 μg–10 mg preferably, 200 μg–2000 μg. The overall daily dose and the metered dose delivered by capsules and cartridges in an inhaler or insulator will generally be double those with aerosol formulations.

Local preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms ie. tablets and capsules. Such dosage unit forms contain from 0.1 mg to 20 mg preferably from 2.5 to 10 mg of the compounds of the invention.

The compounds according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5–30 mg, dependent on the condition being treated, and the duration of treatment desired.

Slow release or enteric coated formulations may be advantageous, particularly for the treatment of inflammatory bowel disorders.

The pharmaceutical compositions according to the invention may also be used in combination with another therapeutically active agent, for example, β-adrenoreceptor agonist, an anti-histamine or an anti-allergic. The invention thus provides, in a further aspect, a combination comprising a compound of formula (I) or a physiologically acceptable solvate thereof with another therapeutically active agent, for example, a β$_2$-adrenoreceptor agonist, an anti-histamine or an anti-allergic.

The combination referred to above may conveniently be presented for use in the form of a pharmaceutical formulation and thus pharmaceutical formulations comprising a combination as defined above together with a pharmaceutically acceptable carrier thereof represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

The compounds of formula (I) and solvates thereof may be prepared by the methodology described, hereinafter, constituting a further aspect of this invention. The novel compounds of formula (II) form yet a further aspect of the present invention.

Thus, according to a first process (A), a compound of formula (I) may be prepared by treating a compound of formula (II)

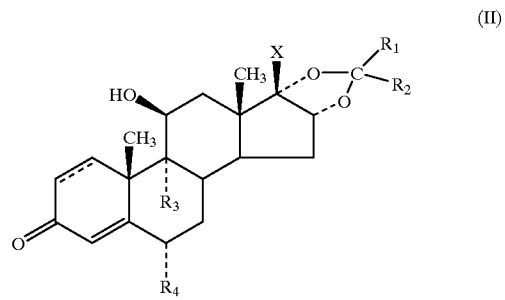

(II)

in which $R_1$, $R_2$, $R_3$, $R_4$ and

----- are hereinbefore described and X is a suitable group such as a thiohydroxamate ester, for example, 2-thioxo-2H-pyridin-1-yloxycarbonyl, 2-thioxo4-methyl-3H-thiazol-3-yloxycarbonyl or 2-thioxo4-phenyl-3H-thiazol-3-yloxycarbonyl, with a compound of formula (III)

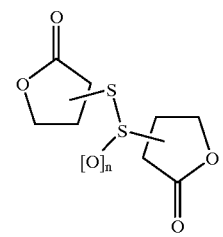

(III)

in which n is 0 or 2.

The radical reaction to introduce the lactone group may be carried out by irradiating a compound of formula (II) in the presence of a compound of formula (III) in an inert solvent such as N,N-dimethylformamide, toluene or dichloromethane, conveniently at a low temperature such as about 0° C. and preferably under an inert atmosphere such as nitrogen or the like. Any suitable radiation source may be used, for example, 200 W tungsten filament light bulbs. Alternatively the radical reaction to introduce the lactone group may be carried out by heating a compound of formula (II) in the presence of a compound of formula (III) in an inert solvent such as N,N-dimethylformamide or toluene at elevated temperatures e.g. 80–90° C., in the presence of a radical initiator, such as AIBN, and in the absence of light, and preferably under an inert atmosphere such as nitrogen or the like.

Compounds of formula (I) may also be prepared from other compounds of formula (I) using conventional interconversion procedures, including transacetalisation. A process for preparing a compound of formula (I) by interconversion of another compound of formula (I) (process B) constitutes yet a further aspect of the present invention.

Compounds of formula (I) having a 1, 2 single bond may be prepared by partial reduction of the corresponding 1, 2 double bond compound by conventional methods. Thus, for example, by hydrogenation of the corresponding compound of formula (I) or of an intermediate used for the preparation of a compound of formula (I) using a palladium catalyst, conveniently in a suitable solvent e.g. ethyl acetate or preferably by using tris(triphenylphosphine) rhodium (I) chloride (known as Wilkinson's catalyst), conveniently in a suitable solvent such as toluene, ethyl acetate or ethanol.

It will be appreciated by those skilled in the art that it may be desirable to use protected derivatives of the intermediates used in the preparation of compounds of formula (I). Thus, the processes described herein may require deprotection as an intermediate or final step to yield the desired compound. Thus, according to another process (C), a compound of formula (I) may be prepared by subjecting a protected derivative of a compound of formula (I) to reaction to remove the protecting group or groups present, constituting a further aspect of the present invention.

Protection and deprotection of functional groups may be effected using conventional means. Thus, hydroxyl groups may be protected using any conventional hydroxyl protecting group, for example, as described in Protective Groups in Organic Chemistry, Ed. J. F. W. McOmie (Plenum Press, 1973) or Protective Groups in Organic Synthesis by Theodora W. Green (John Wiley and Sons, 1991).

Examples of suitable hydroxyl protecting groups includes groups selected from alkyl (e.g. t-butyl or methoxymethyl), aralkyl (e.g. benzyl, diphenylmethyl or triphenylmethyl), heterocyclic groups such as tetrahydropyranyl, acyl (e.g. acetyl or benzoyl) and silyl groups such as trialkylsilyl (e.g. t-butyldimethylsilyl). The hydroxyl protecting groups may be removed by conventional techniques. Thus, for example alkyl, silyl, acyl and heterocyclic groups may be removed by solvolysis, e.g. by hydrolysis under-acidic or basic conditions. Aralkyl groups such as triphenylmethyl may be similarly be removed by solvolysis, e.g. by hydrolysis under acidic conditions. Aralkyl groups such as benzyl may be cleaved by hydrogenolysis in the presence of a Noble metal catalyst such as palladium-on-charcoal.

Compounds of formula (II) and (III) are either generally known compounds or may be prepared by methods analogous to those described in the art for preparing the known compounds of formula (II) and (III) or by the methods described herein. Novel compounds of formula (II) and (III) form yet a further aspect of the present invention.

Thus, a compound of formula (II) may be prepared from a compound of formula (IV)

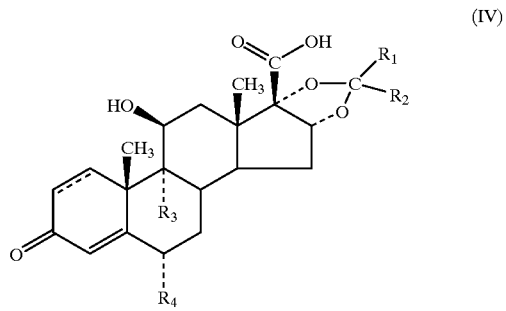

(IV)

(wherein $R_1$, $R_2$, $R_3$, $R_4$ and ----- are as defined hereinbefore) by application or adaptation of known methods for activation of carboxylic acids, for example, the methods described by Kertez and Marx, Journal of Organic Chemistry, 1986, 2315–2328.

Thus, for example, a compound of formula (I) may be prepared by reacting a compound of formula (IV) with an appropriate activating agent such as diethylchlorophosphate in the presence of a base such as a tertiary amine e.g. triethylamine in an inert solvent such as tetrahydrofuran, diethyl ether or dichloromethane, conveniently at room temperature and under an inert atmosphere such as nitrogen, and optionally in the presence of powdered molecular sieves to form an activated intermediate such as a diethylphosphate mixed anhydride of formula (V)

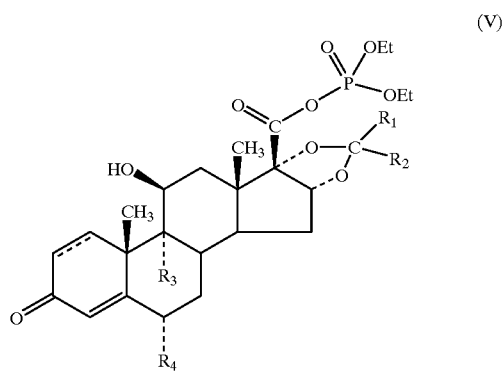

(V)

(wherein $R_1$, $R_2$, $R_3$, $R_4$ and ----- are as defined hereinbefore).

The activated intermediate, which may be isolated if required, may then be reacted with a thiol such as 2-mercaptopyridine-N-oxide sodium salt, 3-hydroxy-4-methylthiazole-2(3H-thione or 3-hydroxy-4-phenylthiazole-2(3H)-thione conveniently under an inert atmosphere such as nitrogen and protected from light to form the desired compound of formula (II). It will be appreciated by those skilled in the art that the activated intermediate need not be isolated if the thiol is present during or added following activation.

Compounds of formula (III) may be prepared by the methods described by Reppe et al. in Justus Liebigs Ann. Chem. 1955, 596, 187 or by oxidation of the corresponding thiol lactone such as β-mercapto-γ-butyrolactone using a suitable oxidising agent such as a halogen e.g. iodine. β-Mercapto-γ-butyrolactone may be prepared by the method described by G. Fuchs, Ark. Kemi, 1968, 29, 379.

A compound of formula (IV) may be prepared by oxidation of a compound of formula (VI)

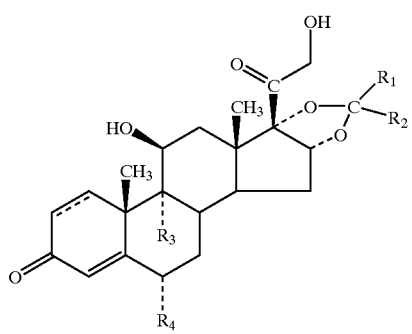

(VI)

(wherein $R_1$, $R_2$, $R_3$, $R_4$ and

===== are hereinbefore defined) by application or adaptation of known methods, for example, methods of the type described Kertesz and Marx, Journal or Organic Chemistry, 1986, 51, 2315–2328.

Compounds of formula (VI) are either commercially available, for example fluocinolone acetonide, budesonide and triamcinolone acetonide are available from Sigma-Aldrich, or can be prepared from the commercially available compounds of formula (VI) by, for example, the transacetalisation methods described in EP0262108 and by partial reduction of the 1,2 double bond compounds by the methods described herein.

Novel compounds of formulas (IV), (V) and (VI) form yet a further aspect of the present invention.

Individual isomers of formula (I) at the point of attachment of the lactone moiety may either be prepared from starting materials having the desired stereochemistry or by epimerisation, resolution or chromatography (e.g. HPLC separation) at an appropriate stage in the synthesis of the required compounds of formula (I) using conventional means.

Thus, for example, it will be appreciated that synthesis employing a diastereoisomeric mixture of compounds of formula (III) will afford compounds of formula (I) as a mixture of diastereoisomers, which may then be separated by conventional methods, such as chromatography or fractional recrystallisation. Alternatively, the individual diastereoisomers may be prepared by employing compounds of formula (III) as (R,R) or (S,S) enantiomers.

A preferred epimerisation method involves the conversion of one or a mixture of diastereoisomers of formula (I) into a mixture which is enriched in another diastereoisomer by a hydrolysis/re-lactonisation procedure. Thus, for example, the lactone group of a compound of formula (I) may be hydrolysed by a base such as sodium hydroxide to form an open chain hydroxy-acid salt, which may be isolated if required, followed by re-lactonisation using for example a suitable acid to give material enriched in one diastereoisomer.

Similarly, compounds of formula (I) in which $R_1$ and $R_2$ are different, may exist in the R and S diastereoisomeric forms. Synthesis of such compounds may be stereospecific to yield individual diastereoisomers. Thus, for example, the R-diastereoisomer of a compound of formula (I) wherein $R_1$ represents H and $R_2$ represents n-propyl may be conveniently prepared by transacetalisation of the corresponding 16α, 17α-isopropylidenedioxy derivative with butyraldehyde in the presence of an acid catalyst, such as perchloric acid, as described in EP0262108. The transacetalisation reaction may be performed at an intermediate stage or after introduction of the lactone group.

Solvates (e.g. hydrates) of a compound of formula (I) may be formed during work-up procedure of one of the aforementioned process steps. Thus, the compounds of formula (I) may be isolated in association with solvent molecules by crystallisation from or evaporation of an appropriate solvent to give the corresponding solvates.

The following Examples illustrate the invention but do not limit the invention in any way.

EXAMPLES

General

Melting points were determined on a Kofler block and are uncorrected. $^1$H-nmr spectra were recorded at 250 or 400 MHz and the chemical shifts are expressed in ppm relative to tetramethylsilane. The following abbreviations are used to describe the multiplicities of the signals: s (singlet), d (doublet), t (triplet), q (quartet), m (multiplet), dd (doublet of doublets), dt (doublet of triplets) and br (broad). MS(TSP+ve) and MS(ES+ve) refer to mass spectra run in positive mode using thermospray or electrospray techniques respectively. TLC (thin layer chromatography) was performed on Merck Kieselgel 60 $F_{254}$ plates and column chromatography was performed on Merck Kieselgel 60 (Art. 7734 or 9385). Preparative HPLC (high performance liquid chromatography) was performed on a Gilson Medical Electronics system using the stationary phase indicated in the example. DMF is used as an abbreviation for anhydrous N,N-dimethylformamide. Organic solutions were dried over anhydrous magnesium sulphate.

Where mixtures of isomers resulting from the asymmetric centre in the lactone group have been prepared, these isomers may be separated by conventional chromatography on silica and assigned as isomers A and B respectively in order of elution from the column.

Intermediate 1

16α,17α-(R-Butylidenedioxy)-6α,9α-difluoro-11β-hydroxy-3-oxo-androsta-1,4-diene-17β-carboxylic acid diethyl phosphoric anhydride A solution of 16α,17α-(R-butylidenedioxy)-6α,9α-difluoro-11β-hydroxy-3-oxo-androsta-1,4-diene-17β-carboxylic acid (4 g, 8.84 mmol) in tetrahydrofuran (100 ml) was treated with 4A powdered molecular sieves (3 g), followed by triethylamine (2.64 ml, 17.68 mmol) and the mixture was stirred for 2 h under nitrogen at 20° C. Diethyl chlorophosphate (1.92 ml, 13.26 mmol) was then added and the reaction mixture was stirred for a further 16 h at 20° C. The reaction mixture was filtered and the filtrate was concentrated. The residue was dissolved in ethyl acetate (150 ml) and washed with 1 M hydrochloric acid (2×100 ml), aq. potassium carbonate, water and brine (100 ml each). The organic phase was dried (MgSO$_4$) and the solvent was removed under reduced pressure, to give the title compound (4.354 g, 84%): MS (TSP+ve) m/z 589 (M+H)$^+$; NMR δ (CDCl$_3$) includes 7.16 (1 H, d, J 10 Hz), 6.44 (1 H, s), 6.37 (1 H, d, J 10 Hz), 5.49 and 5.29 (1 H, 2 m), 5.00 (1 H, d, J 5 Hz), 4.78 (1 H, t, J 4 Hz). 4.47–4.02 (5 H, m), 1.55 (3 H, s), 1.39 (6 H, t, J 7 Hz), 1.08 (3 H, s), 0.90 (3 H, t, J 7.5 Hz).

Intermediate 2

16α,17α-(R-Butylidenedioxy)-6α,9α-difluoro-11β-hydroxy-3-oxo-androsta-1,4-diene-17β-carboxylic acid, 2-thioxo-2H-pyridin-1-yl ester A solution of 16α,17α-(R-butylidenedioxy)-6α,9α-difluoro-11β-hydroxy-3-oxo-androsta-1,4-diene-17β-carboxylic acid diethyl phosphoric anhydride (Intermediate 1, 1 g, 1.7 mmol) in DMF (8.5 ml) in a flask protected from light (aluminium foil) was treated with 2-mercaptopyridine-N-oxide sodium salt (304 mg, 2.04 mmol) at 20° C. under nitrogen for 16 h. The reaction mixture was then poured into ethyl acetate (100 ml) and the mixture was washed with brine (100 ml), water (3×100 ml), sat. sodium bicarbonate, water and brine (100 ml each). The organic phase was dried (MgSO$_4$), the solvent was removed under reduced pressure, and the residue was purified by HPLC (diol column 25 cm×5 cm) eluting with 90% ethyl acetate-heptane to give the title compound (580 mg, 61%): MS (TSP+ve) m/z 562 (M+H)$^+$; IR $\nu_{max}$ (KBr) 3443, 1788, 1736, 1705, 1670, 1633, 1606, 1527 cm$^{-1}$; NMR δ (DMSO-d$_6$) includes 8.24 (1 H, d, J 7 Hz), 7.60 (1 H, d, J 8 Hz), 7.67 (1 H, t, J 8 Hz), 7.29 (1 H, d, J 10 Hz), 6.94 (1 H,. t, J 7 Hz), 6.31 (1 H, d, J 10 Hz), 6.13 (1 H, s), 5.73 and 5.56 (1 H, 2 m), 5.58 (1 H, brs), 5.22 (1 H, t, J 4 Hz), 5.02 (1 H, d, J 5 Hz), 4.24 (1 H, m), 1.51 (3 H, s), 1.15 (3 H, s), 0.89 (3 H, t, J 7.5 Hz). (Found: C, 61.06; H, 6.21; N, 2.05; S, 5.00. C$_{29}$H$_{33}$F$_2$NO$_6$S.C$_4$H$_8$O$_2$ requires C, 61.00; H, 6.36; N, 2.16; S, 4.93%).

Intermediate 3

16α,17α-(R-Butylidenedioxy)-6α,9α-difluoro-11β-hydroxy-3-oxo-androst-4-ene-17β-carboxylic acid A solution of 16α,17α-(R-butylidenedioxy)-6α,9α-difluoro-11β-hydroxy-3-oxo-androsta-1,4-diene-17β-carboxylic acid (4.66 g, 10.3 mmol) in ethanol (180 ml) was hydrogenated over tris(triphenylphosphine)rhodium (I) chloride (466 mg) at atmospheric pressure for 65 h. A further quantity of catalyst (500 mg) was added and the reaction mixture was hydrogenated for a further 48 h. The mixture was filtered through celite and the filtrate was concentrated. The residue was dissolved in ethyl acetate (150 ml) and extracted with aq. potassium carbonate (3×100 ml). The combined aq. extracts were washed with ethyl acetate (100 ml) and acidified to pH 2 with 7 M hydrochloric acid. The resulting suspension was extracted with ethyl acetate (3×100 ml) and the combined organic extracts were washed with water (2×100 ml) and brine (2×150 ml). The organic phase was dried (MgSO$_4$) and the solvent was removed under reduced pressure, to give the title compound (3.932 g, 84%): mp 145–150° C.; MS (TSP+ve) m/z 455 (M+H)$^+$; IR $\nu_{max}$ (KBr) 3443,1736,1654,1649 cm$^{-1}$; NMR δ (DMSO-d$_6$) includes 5.81 (1 H, s), 5.60 and 5.41 (1 H, 2 m), 5.17 (1 H, br s), 4.87 (1 H, br s), 4.68 (1 H, t, J 4 Hz), 4.15 (1 H, m), 1.49 (3 H, s), 0.93 (3 H, s), 0.87 (3 H, t, J 7 Hz). (Found: C, 61.01; H, 7.29. C$_{24}$H$_{32}$F$_2$O$_6$.H$_2$O requires C, 61.00; H, 7.25%).

Intermediate 4

16α,17α-(R-Butylidenedioxy)-6α,9α-difluoro-11β-hydroxy-3-oxo-androst-4-ene-17β-carboxylic acid diethyl phosphoric anhydride A solution of 16α,17α-(R-butylidenedioxy)-6α,9α-difluoro-11β-hydroxy-3-oxo-androst-4-ene-17β-carboxylic acid (Intermediate 3, 3 g, 6.6 mmol) in tetrahydrofuran (75 ml) was treated with 4A powdered molecular sieves (2 g), followed by triethylamine (1.38 ml, 9.9 mmol) and the mixture was stirred for 1.5 h under nitrogen at 20° C. Diethyl chlorophosphate (1.05 ml, 7.26 mmol) was then added and the reaction mixture was stirred for a further 16 h at 20° C. The reaction mixture was filtered and the filtrate was concentrated. The residue was dissolved in ethyl acetate (120 ml) and washed with 2 M hydrochloric acid (2×100 ml), aq. potassium carbonate, water and brine (100 ml each). The organic phase was dried (MgSO$_4$) and the solvent was removed under reduced pressure, to give the title compound (3.342 g, 86%): MS (ES+ve) m/z 591 (M+H)$^+$; IR $\nu_{max}$ (KBr) 1767, 1668 cm$^{-1}$; NMR δ (CDCl$_3$) includes 6.14 (1 H, s), 5.37 and 5.18 (1 H, 2 m), 5.10 (1 H, d, J 5 Hz), 4.79 (1 H, t, J 4.5 Hz), 4.4–4.2 (5 H, m), 1.53 (3 H, s), 1.39 (6 H, t, J 7 Hz), 1.06 (3 H, s), 0.93 (3 H, t, J 7 Hz). (Found: C, 56.99; H, 7.08. C$_{28}$H$_{41}$F$_2$O$_9$P requires C, 56.94; H, 7.00%).

Intermediate 5

16α,17α-(R-Butylidenedioxy)-6α,9α-difluoro-11β-hydroxy-3-oxo-androst-4-ene-17β-carboxylic acid, 2-thioxo-2H-pyridin-1-yl ester A solution of 16α,17α-(R-butylidenedioxy)-6α,9α-difluoro-11β-hydroxy-3-oxo-androst-4-ene-17β-carboxylic acid diethyl phosphoric anhydride (Intermediate 4, 1.5 g, 2.54 mmol) in DMF (12 ml) in a flask protected from light (aluminium foil) was treated with 2-mercaptopyridine-N-oxide sodium salt (455 mg, 3.05 mmol) at 20° C. under nitrogen for 20 h. The reaction mixture was then poured into ethyl acetate (150 ml) and the mixture was washed with brine (100 ml), water (2×100 ml), sat. sodium bicarbonate, water and brine (100 ml each). The organic phase was dried (MgSO$_4$) and the solvent was removed under reduced pressure, to give the title compound (1.25 g, 87%): MS (TSP+ve) m/z 564 (M+H)$^+$; IR $\nu_{max}$ (KBr) 3412, 1800, 1718, 1684, 1669, 1609, 1527 cm$^{-1}$; NMR δ (DMSO-d$_6$) includes 8.23 (1 H, d, J 7 Hz), 7.6 (1 H, dd, J 9 and 2 Hz), 7.46 (1 H, dt, J 7 and 2 Hz), 6.93 (1 H, dt, J 7 and 2 Hz), 5.83 (1 H, s), 5.62 and 5.43 (1 H, 2 m), 5.28 (1 H, d, J 4.5 Hz), 5.24 (1 H, t, J 4.5 Hz), 5.0 (1 H, d, J 4.5 Hz), 4.26–4.16 (1 H, m), 1.51 (3 H, s), 1.14 (3 H, s), 0.91 (3 H, t, J 7.5 Hz). (Found: C, 61.63; H, 6.46; N, 2.16; S, 5.23. C$_{29}$H$_{35}$F$_2$NO$_6$S.0.3C$_4$H$_8$O$_2$ requires C, 61.47; H, 6.39; N, 2.37; S, 5.43%).

Intermediate 6

6α,9α-Difluoro-11β-hydroxy-16α,17α-isopropylidenedioxy-3-oxo-androst-4-ene-17β-carboxylic acid diethyl phosphoric anhydride A solution of 6α,9α-difluoro-11β-hydroxy-16α,17α-isopropylidenedioxy-3-oxo-androst-4ene-17β-carboxylic acid (3 g, 6.81 mmol) in tetrahydrofuran (75 ml) was treated with 4A powdered molecular sieves (2 g), followed by triethylamine (1.42 ml, 10.21 mmol) and the mixture was stirred for 2 h under nitrogen at 20° C. Diethyl chlorophosphate (1.08 ml, 7.49 mmol) was then added and the reaction mixture was stirred for a further 20 h at 20° C. The reaction mixture was filtered and the filtrate was concentrated. The residue was dissolved in ethyl acetate (120 ml) and washed with 2 M hydrochloric acid, water, aq. potassium carbonate, water and brine (100 ml each). The organic phase was dried (MgSO$_4$) and the solvent was removed under reduced pressure, to give the title compound (3.637 g, 92%): MS (TSP+ve) m/z 577 (M+H)$^+$; IR $\nu_{max}$ (KBr) 3418, 1768, 1683, 1669 cm$^{-1}$; NMR δ (CDCl$_3$) includes 6.14 (1 H, s), 5.37 and 5.18 (1 H, 2 m), 5.12 (1 H, d, J 4.5 Hz), 4.41–4.19 (5 H, m), 1.52 (3 H, s), 1.48 (3 H, s), 1.39 (3 H, t, J 6.5 Hz), 1.38 (3 H, t, J 6.5 Hz), 1.28 (3 H, s), 1.05 (3 H, s). (Found: C, 55.80; H, 6.91. C$_{27}$H$_{39}$F$_2$O$_9$P.0.18C$_4$H$_8$O$_2$.0.2H$_2$O requires C, 55.86; H, 6.91%).

Intermediate 7

6α,9α-Difluoro-11β-hydroxy-16α,17α-isopropylidenedioxy-3-oxo-androst-4-ene-17β-carboxylic acid, 2-thioxo-2H-pyridin-1-yl ester A solution of 6α,9α-difluoro-11β-hydroxy-16α,17α-isopropylidenedioxy-3-oxo-androst-4-ene-17β-carboxylic acid diethyl phosphoric anhydride (Intermediate 6, 1.5 g, 2.6 mmol) in DMF (12 ml) in a flask protected from light (aluminium foil) was treated with 2-mercaptopyridine-N- oxide sodium salt (465 mg, 3.12 mmol) at 20° C. under nitrogen for 16 h. The reaction mixture was then poured into ethyl acetate (200 ml) and the mixture was washed with brine (150 ml), water (3×50 ml), and brine (2×50 ml). The organic phase was dried (MgSO$_4$) and the solvent was removed under reduced pressure to give the title compound (1.128 g, 79%): MS (TSP+ve) m/z 550 (M+H)$^+$; IR $\nu_{max}$ (KBr) 3391, 1805, 1715, 1669, 1654, 1612 cm$^{-1}$; NMR δ (DMSO-d$_6$) includes 7.92 (1 H, d, J 6 Hz), 7.60 (1 H, d, J 8 Hz), 7.45 (1 H, t, J 8 Hz), 6.88 (1 H m), 5.83 (1 H, s), 5.62 and 5.43 (1 H, 2 m), 5.33 (1 H, d, J 5 Hz), 5.13 (1 H, br s), 4.21 (1 H, m), 1.51, 1.43, 1.39 and 1.19 (4 s, 3 H each) (Found: C, 58.80; H, 5.91; N, 2.50; S. 5.18. $C_{28}H_{33}F_2NO_6S1.1H_2O.0.15C_3H_7NO$ requires C, 58.87; H, 6.30; N, 2.78; S, 5.52%).

Intermediate 8
4,4'-Disulfanediylbis(dihydro-furan-2-one)

A solution of β-mercapto-γ-butyrolactone (106 mg, 0.9 mmol) in dichloromethane (2 ml) was treated with a solution of iodine (253 mg, 1 mmol) in dichloromethane (5 ml) and the mixture was stirred for 18 h at 20° C. The reaction mixture was diluted with dichloromethane and washed with aqueous sodium metabisulfite solution, dried (MgSO$_4$), the solvent was removed under reduced pressure, and the residue was purified by preparative TLC on a single plate (20 cm×20 cm) run in ethyl acetate-cyclohexane (2:1) to give the title compound (30 mg, 28%):. MS (TSP+ve) m/z 252 (M+NH$_4$)$^+$; IR $\nu_{max}$ (KBr) 1778, 1771, 1164, 1023, 989, 843 cm$^{-1}$; NMR δ (CDCl$_3$) 4.6 (2 H, dd, J 9 and 6 Hz), 4.35 (2 H, dt, J 5 and 4 Hz), 3.86–3.72 (2 H, m), 2.96 (2 H, dd, J 17 and 8 Hz), 2.66 (2 H, dt, J 18 and 5 Hz); HRMS (EI) found: 234.0017. $C_8H_{10}O_4S_2$ requires 234.0020.

Example 1
16α,17α-(R-Butylidenedioxy)-6α,9α-difluoro-11β-hydroxy-17β-(2-oxo-tetrahydro furan-3-yl-sulfanyl)-androsta-1,4-dien-3-one A solution of 16α,17α-(R-butylidenedioxy)-6α,9α-difluoro-11β-hydroxy-3-oxo-androsta-1,4-diene-17β-carboxylic acid, 2-thioxo-2H-pyridin-1-yl ester (Intermediate 2, 300 mg, 0.53 mmol) in dry DMF (5.5 ml) was added to a stirred solution of 3,3'-disulfanediylbis (dihydro-furan-2-one) (also known as (γ-butyrolactone) disulphide) (199 mg, 1.07 mmol) in dry DMF (2 ml) under nitrogen at 0° C. The reaction mixture was protected from light and stirred under vacuum for a few minutes. The mixture was then placed under an atmosphere of nitrogen and while still at 0° C. was subjected to irradiation by two 200 W tungsten filament light bulbs for approximately 16 h. The reaction mixture was diluted with ethyl acetate (125 ml) and washed with brine, water, 2M hydrochloric acid, water, sat. sodium bicarbonate, water and brine (100 ml each). The organic solution was dried (MgSO$_4$), the solvent was removed under reduced pressure, and the residue was purified by reversed phase HPLC (Dynamax C18 column, 25 cm×5 cm) eluting with 65% acetonitrile-water, flow rate 45 ml/min and detecting at 240 nm. Appropriate fractions were combined and evaporated under reduced pressure. The residue was dissolved in ethyl acetate (50 ml) and the solution was dried (MgSO$_4$) and evaporated to give the title compound isomer A (75 mg, 27%): mp 183–185° C.; MS (TSP+ve) m/z 525 (M+H)$^+$; IR $\nu_{max}$ (KBr) 1772, 1669, 1630, 1611 cm$^{-1}$; NMR δ (CDCl$_3$) includes 7.13 (1 H, d, J 10 Hz), 6.43 (1 H, s), 6.37 (1 H, d, J 10 Hz), 5.48 and 5.28 (1 H, 2 m), 5.26 (1 H, t, J 4.5 Hz), 4.41–4.21 (4 H, m), 3.85 (1 H, t, J 8.5 Hz), 1.54 (3 H, s), 1.29 (3 H, s), 0.94 (3 H, t, J 7.5 Hz). (Found: C, 61.59; H, 6.73; S, 6.07. $C_{27}H_{34}F_2O_6S$ requires C, 61.82; H, 6.53; S, 6.11%), and the title compound isomer B (83.3 mg, 30%): mp 204–207° C.; MS (TSP+ve) m/z 525 (M+H)$^+$; IR $\nu_{max}$ (KBr) 1774, 1668, 1628, 1609 cm$^{-1}$; NMR δ(CDCl$_3$) includes 7.08 (1 H, d, J 10 Hz), 6.44 (1 H, s), 6.37 (1 H, d, J 10 Hz), 5.45 (1 H, t, J 4.5 Hz), 5.47 and 5.28 (1 H, 2 m), 4.80–4.21 (4 H, m), 3.81 (1 H, t, J 8.5 Hz), 1.54 (3 H, s), 1.19 (3 H, s), 0.93 (3 H, t, J 7.5 Hz). (Found: C, 61.05; H, 6.68; S, 5.76. $C_{27}H_{34}F_2O_6S.0.5C_4H_8O_2$ requires C, 61.25; H, 6.74; S, 5.64%).

Example 2
6α,9α-Difluoro-11β-hydroxy-16α,17α-isopropylidenedioxy-17β-(2-oxo-tetrahydro-furan-3-yl-sulfanyl)-androsta-1,4-dien-3-one Method 1

A solution of 6α,9α-difluoro-11β-hydroxy-16α,17α-isopropylidenedioxy-3-oxo-androsta-1,4-diene-17β-carboxylic acid, 2-thioxo-2H-pyridin-1-yl ester (2.504 g, 4.57 mmol) in dry DMF (15 ml) was added to a stirred suspension of 3,3'-disulfanediylbis (dihydro-furan-2-one) (also known as (γ-butyrolactone) disulphide) (2.148 g, 9.17 mmol) in dry DMF (15 ml) under nitrogen at 0° C. and then subjected to irradiation by two 200 W tungsten filament light bulbs for approximately 4 h. The reaction mixture was diluted with ethyl acetate (650 ml) and washed with brine, water, 2M hydrochloric acid, water, sat. sodium bicarbonate, water and brine (200 ml each). The organic solution was dried (MgSO$_4$), the solvent was removed under reduced pressure, and the residue was chromatographed on silica gel eluting with chloroform-methanol (50:1) and further purified by reversed phase HPLC (Dynamax C18 column, 25 cm×5 cm) eluting with 60% acetonitrile-water, flow rate 45 ml/min and detecting at 240 nm. Appropriate fractions were combined and evaporated under reduced pressure. The residue was dissolved in ethyl acetate (50 ml), the solution was dried (MgSO$_4$), evaporated, and triturated in diethyl ether to give the title compound isomer A (602 mg, 26%): mp 262–275° C.; MS (TSP+ve) m/z 511 (M+H)$^+$; IR $\nu_{max}$ (KBr) 3461, 1768, 1668, 1633 cm$^{-1}$; NMR δ (CDCl$_3$) includes 7.25 (1 H, dd, J 10 and 1 Hz), 6.43 (1 H, s), 6.37 (1 H, dd, J 10 and 2 Hz), 5.46 and 5.33 (1 H, 2 m), 4.56 (1 H, t, J 3 Hz), 4.38–4.26 (3 H, m), 3.88 (1 H, t, J 8 Hz), 1.62, 1.54, 1.44, 1.27 (4 s, 3 H each). (Found: C, 60.8; H, 6.6; S, 5.7. $C_{26}H_{32}F_2O_6S.0.6C_4H_{10}O.0.5H_2O$ requires C, 60.5; H, 7.0; S, 5.7%), and the title compound isomer B (635 mg, 27%): mp 296–302° C.; MS (TSP+ve) m/z 511 (M+H)$^+$; IR $\nu_{max}$ (KBr) 3461, 1774, 1668, 1629 cm$^{-1}$; NMR δ (CDCl$_3$) includes 7.08 (1 H, dd, J 10 and 1 Hz), 6.45 (1 H, s), 6.38 (1 H, dd, J 10 and 2 Hz), 5.45 and 5.35 (1 H, 2 m), 4.7 (1 H, t, J 3 Hz), 4.43–4.26 (3 H, m), 3.93 (1 H, t, J 8 Hz), 1.69, 1.52, 1.44, 1.20 (4 s, 3 H each). (Found: C, 61.2; H, 6.1; S, 6.1. $C_{26}H_{32}F_2O_6S$ requires C, 61.15; H, 6.3; S, 6.3%).

The configuration of isomer B was shown to be S at the lactone asymmetric centre by an X-ray diffraction study.

Method 2

A solution of 6α,9α-difluoro-11β-hydroxy-16α,17α-isopropylidenedioxy-17β-(2-oxo-tetrahydro-furan-3-yl-sulfanyl)-androsta-1,4-dien-3-one (Example 2, isomer B) (100 mg, 0.19 mmol) in tetrahydrofuran (3 ml) was treated with sodium hydroxide (1 M, 0.19 ml) and the mixture was stirred for 2 h at 20° C. The reaction mixture was evaporated to dryness under reduced pressure, the residue was dissolved in water (16 ml) and washed with diethyl ether (35 ml) and ethyl acetate (25 ml). The aqueous phase was then freeze-dried to give 2-(6α,9α-difluoro-11β-hydroxy-16α,17α-isopropylidenedioxy-3-oxo-androsta-1,4-dien-17β-ylsulfanyl)-4-hydroxybutanoic acid, sodium salt (76 mg, 70%): MS (ES+ve) m/z 529 (M+H)$^+$, 551 (M+Na)$^+$; NMR δ (DMSO-$d_6$) includes 7.28 (1 H, d, J 10 Hz), 6.25 (1 H, dd, J 10 and 2 Hz), 6.10 (1 H, s), 5.69 and 5.56 (1 H, 2 m), 4.50 (0.1 H, d, J, 5 Hz), 4.31 (0.9 H, d, J 5 Hz), 4.12 (1 H, m), 3.65 (1 H, dd, J 9 and 3 Hz), 3.55 (1 H, m), 3.42 (1 H, m), 1.55, 1.50, 1.28, 1.17 (4 s, 3 H each); HPLC RT 6.077 min, 10% (isomer B) and 6.264 min, 79.5% (isomer A) [Phenomenex Prodigy ODS-2 column (15 cm×0.46 cm) eluting with 15–95% $CH_3CN/H_2O$ over 16 min]. (Found: C, 51.8; H, 6.5; S, 5.6 $C_{26}H_{33}F_2O_7SNa$ requires C, 51.7; H, 6.5; S, 5.3%)

Acidification of the 2-(6α,9α-difluoro-11β-hydroxy-16α,17β-isopropylidenedioxy-3-oxo-androsta-1,4-dien-17β-ylsulfanyl)4-hydroxybutanoic acid, sodium salt with p-toluenesulfonic acid in a mixture of ethyl acetate and 2M hydrochloric acid (1:1) over 18 h gave predominantly lactone isomer A of Example 2 (HPLC RT 8.125 min 63% (isomer A) and 7.747 min 7% (isomer B).

Example 3

16α,17α-(R-Butylidenedioxy)-6α,9α-difluoro-11β-hydroxy-17β-(2-oxo-tetrahydro-furan-3-yl-sulfanyl)-androst-4-en-3-one A solution of 16α,17α-(R-butylidenedioxy)-6α,9α-difluoro-11β-hydroxy-3-oxo-androst-4-ene-17β-carboxylic acid, 2-thioxo-2H-pyridin-1-yl ester (Intermediate 5, 400 mg, 0.71 mmol) in dry DMF (7.5 ml) was added to a stirred solution of 3,3'-disulfanediylbis (dihydro-furan-2-one) (also known as (γ-butyrolactone) disulphide) (264.5 mg, 1.42 mmol) in dry DMF (2.6 ml) under nitrogen at 0° C. The reaction mixture was protected from light and stirred under vacuum for a few minutes. The mixture was then placed under an atmosphere of nitrogen and while still at 0° C. was subjected to irradiation by two 200 W tungsten filament light bulbs for approximately 5 h. The reaction mixture was diluted with ethyl acetate (150 ml) and washed with brine, water, 2M hydrochloric acid, water, aq. potassium carbonate, water and brine (100 ml each). The organic solution was dried ($MgSO_4$), the solvent was removed under reduced pressure, and the residue was purified by reversed phase HPLC (Dynamax C18 column, 25 cm×5 cm) eluting with 65% acetonitrile-water, flow rate 45 ml/min and detecting at 240 nm. Appropriate fractions were combined and evaporated under reduced pressure. The residue was dissolved in ethyl acetate (50 ml) and the solution was dried ($MgSO_4$), evaporated and triturated in diethyl ether to give the title compound isomer A (79.4 mg, 21%): mp 120–122° C.; MS (TSP+ve) m/z 527 (M+H)$^+$; IR $v_{max}$ (KBr) 3480, 1768, 1682, 1668, cm$^{-1}$; NMR δ (CDCl$_3$) includes 6.14 (1 H, s), 5.36 and 5.17 (1 H, 2 m), 5.27 (1 H, t, J 4 Hz), 4.4–4.2 (4 H, m), 3.88 (1 H, t, J 8.5 Hz), 1.53 (3 H, s), 1.27 (3 H, s), 0.97 (3 H, t, J 7.5 Hz). (Found: C, 61.17; H, 6.94; S, 6.18. $C_{27}H_{36}F_2O_6S.0.2H_2O$ requires C, 61.16; H, 6.92; S, 6.05%), and the title compound isomer B (91 mg, 24%): mp 209–213° C.; MS (TSP+ve) m/z 527 (M+H)$^+$; IR $v_{max}$ (KBr) 3493, 1774, 1668 cm$^{-1}$; NMR δ(CDCl$_3$) includes 6.15 (1 H, s), 5.47 (1 H, t, J 4.5 Hz), 5.36 and 5.17 (1 H, 2 m), 4.5–4.2 (4 H, m), 3.84 (1 H, t, J 8.5 Hz), 1.53 (3 H, s), 1.17 (3 H, s), 0.93 (3 H, t, J 7.5 Hz). (Found: C, 61.50; H, 7.36; S, 5.87. $C_{27}H_{36}F_2O_6S.0.25C_4H_{10}O.0.15C_4H_8O_2$ requires C, 61.52; H, 7.17; S, 5.74%).

Example 4

6α,9α-Difluoro-11β-hydroxy-16α,17α-isopropylidenedioxy-17β-(2-oxo-tetrahydro-furan-3-yl-sulfanyl)-androst-4-en-3-one A solution of 6α,9α-difluoro-11β-hydroxy-16α,17α-isopropylidenedioxy-3-oxo-androst-4-ene-17β-carboxylic acid, 2-thioxo-2H-pyridin-1-yl ester (Intermediate 7, 400 mg, 0.73 mmol) in dry DMF (7.5 ml) was added to a stirred suspension of 3,3'-disulfanediylbis (dihydro-furan-2-one) (also known as (γ-butyrolactone) disulphide) (271 mg, 1.45 mmol) in dry DMF (2.7 ml) under nitrogen at 0° C. The mixture was protected from light and degassed by stirring vigorously under vacuum for several minutes. The mixture was then placed under an atmosphere of nitrogen and subjected to irradiation by two 200 W tungsten filament light bulbs for 4.5 h. The reaction mixture was diluted with ethyl acetate (150 ml) and washed with water (3×100 ml), 2M hydrochloric acid, water, aq. potassium carbonate, water and brine (100 ml each). The organic solution was dried ($MgSO_4$), concentrated, purified by reversed phase HPLC (Dynamax C18 column, 25 cm×5 cm) eluting with 60% acetonitrile-water, and further purified by HPLC eluting with 53% acetonitrile-water. Appropriate fractions were combined and evaporated under reduced pressure. The residue was dissolved in ethyl acetate (50 ml) and the solution was dried ($MgSO_4$) and evaporated to give the title compound isomer A (46.6 mg, 12%): mp 258–263° C.; MS (TSP+ve) m/z 513 (M+H)$^+$; IR $v_{max}$ (KBr) 3480, 1772, 1669 cm$^{-1}$; NMR δ (CDCl$_3$) includes 6.14 (1 H, s), 5.38 and 5.19 (1 H, 2 m), 4.57 (1 H, br s), 4.4–4.2 (3 H, m), 3.89 (1 H, t, J 8.5 Hz), 1.64, 1.53 1.48, 1.25 (4 s, 3 H each). (Found: C, 61.04; H, 6.78; S, 6.10. $C_{26}H_{34}F_2O_6S$ requires C, 60.92; H, 6.69; S, 6.25%), and the title compound isomer B (33.1 mg, 9%): mp 237–240° C.; MS (TSP+ve) m/z 513 (M+H)$^+$; IR $v_{max}$ (KBr) 3501, 1774, 1668 cm$^{-1}$; NMR δ (CDCl$_3$) includes 6.14 (1 H, s), 5.37 and 5.18 (1 H, 2 m), 4.68 (1 H, d, J 4.5 Hz), 4.45–4.21 (3 H, m), 3.95 (1 H, t, J 8 Hz), 1.67, 1.53, 1.47, 1.16 (4 s, 3 H each). (Found: C, 61.21; H, 6.72. $C_{26}H_{34}F_2O_6S$ requires C, 60.92; H, 6.69%).

The configuration of isomer B was shown to be S at the lactone asymmetric centre by an X-ray diffraction study.

Example 5

16α,17α-(R-Butylidenedioxy)-6α,9α-difluoro-11β-hydroxy-17β-(2-oxo-tetrahydro-furan-4-yl-sulfanyl)-androst-4-en-3-one A solution of 16α,17α-(R-butylidenedioxy)-6α,9α-difluoro-11β-hydroxy-3-oxo-androst-4-ene-17β-carboxylic acid, 2-thioxo-2H-pyridin-1-yl ester (Intermediate 5, 1.3 g, 2.3 mmol) in dry DMF (13 ml) was added to a stirred solution of 4,4'-disulfanediylbis(dihydro-furan-2-one) (Intermediate 8, 450 mg, 1.92 mmol) in dry DMF (5 ml) under nitrogen at 0° C. The reaction mixture was protected from light and stirred under vacuum for a few minutes. The mixture was then placed under an atmosphere of nitrogen and while still at 0° C. was subjected to irradiation by two 200 W tungsten filament light bulbs for approximately 5 h. The reaction mixture was diluted with ethyl acetate (250 ml) and washed with brine, 2M hydrochloric acid, and brine (100 ml each). The organic solution was dried ($MgSO_4$), the solvent was removed under reduced pressure, and the residue was purified by column chromatography on silica gel eluting with ethyl acetate-cyclohexane (1:1) and then by reversed phase HPLC (Dynamax C18 column, 25 cm×5 cm) eluting with 65% acetonitrile-water, flow rate 45 ml/min and detecting at 230 nm. Appropriate fractions were combined and evaporated under reduced pressure. The first residue was dissolved in ethyl acetate (50 ml) and the solution was dried ($MgSO_4$), evaporated and triturated in diethyl ether to give the title compound isomer A (54 mg, 4%): mp 117–119° C.; MS (TSP+ve) m/z 527 (M+H)$^+$, 443 (MH-$C_4H_4O_2$)$^+$; IR $v_{max}$ (KBr) 3474, 1782, 1667, 1001, 732 cm$^{-1}$; NMR δ (CDCl$_3$) includes 6.15 (1 H, s), 5.37 and 5.18 (1 H, 2 m), 5.22 (1 H, t, J 5 Hz), 4.63 (1 H, dd, J 9 and 8 Hz), 4.37 (1 H, m), 4.24 (1 H, d, J 5 Hz), 4.2–4.1 (1 H, br), 4.14 (1 H, t, J 9 Hz), 4.05–3.88 (1 H, m), 2.85 (1 H, dd, J 17 and 8 Hz), 1.53 (3 H, s), 1.2 (3 H, s), 0.97 (3 H, t, J 8 Hz). (Found: C, 59.56; H, 6.74; S, 5.61. $C_{27}H_{36}F_2O_6S.H_2O$ requires C, 59.54; H, 7.03; S, 5.89%). The second residue was dissolved in dichloromethane (50 ml), the solution was dried (MgSO$_4$), and evaporated to give the title compound isomer B (29 mg, 2%): mp 112–113° C.; MS (TSP+ve) m/z 527 (M+H)$^+$, 443 (MH-C$_4$H$_4$O$_2$)$^+$; IR $\nu_{max}$ (KBr) 1782, 1669, 1280, 736 cm$^{-1}$; NMR δ (CDCl$_3$) includes 6.14 (1 H, s), 5.25 (1 H, t, J 4 Hz), 5.35 and 5.17 (1 H, 2 m), 4.58 (1 H, dd, J 9 and 7 Hz), 4.37 (1 H, m), 4.28 (1 H, d, J 5 Hz), 4.05 (1 H, t, J 9 Hz), 4.0–3.86 (1 H, m), 2.93 (1 H, dd, J 18 and 8 Hz), 2.62 (1 H, dd, J 18 and 9 Hz), 1.53 (3 H, s), 1.17 (3 H, s), 0.96 (3 H, t, J 7 Hz). (Found: C, 57.94; H, 6.43; S, 5.28. $C_{27}H_{36}F_2O_6S.0.5CH_2Cl_2$ requires C, 58.04; H, 6.55; S, 5.63%).

Pharmacological Activity

In Vitro

The pharmacological activity was studied in a functional in vitro assay to demonstrate glucocorticoid activity which is generally predictive of anti-inflammatory or anti-allergic activity in-vivo.

The functional assay used was a modification of the method described by T. S Berger et al, of J. of Steroid Biochem. Molec. Biol. 1992, 41 (3–8), 733–738, "Interaction of Glucocorticoid analogues with the Human Glucocorticoid Receptor"

Thus, Hela cells were stably transfected with a detectable reporter gene (secreted placental alkaline phosphatase, sPAP) under the control of a glucocorticoid response promoter (the LTR of the mouse mammary tumour virus, MMTV).

Various concentrations of standard (dexamethasone) or compounds of the invention were incubated with transfected Hela cells for 72 hours. At the end of the incubation, substrate (p-nitrophenol acetate) for sPAP was added and the product measured by a spectrophotometric method. Increased absorbance reflected increased sPAP transcription and concentration-response lines were constructed such that $EC_{50}$-values could be estimated.

In this test, the isomers of the Examples 1 to 5 had $EC_{50}$-values of less than 200 nM.

Hydrolysis in Blood

All the isomers of the Examples were unstable in human plasma (half-lives less than 60 min), indicating that they are expected to possess an advantageous in vivo side effect profile.

In Vivo (i) Anti-Inflammatory Activity—Inhibition of Rat Ear Oedema

The test compounds are dissolved in acetone and 40ul containing 5% croton oil is applied to the inner surface of each of the ears of 60–80 g male rats. Animals are killed 6 hours later and the ears are removed. Standard size (0.5 cm diameter) discs are punched out and the discs weighed. Mean weight of the ear discs is calculated and from this percentage inhibition of ear inflammation in relation to croton oil alone treated ears are calculated.

| Compound | Dose | % Inhibition |
|---|---|---|
| Example 2 Isomer A | 100 µg | 56 |
| Example 2 Isomer B | 100 µg | 54 |
| Example 3 Isomer A | 100 µg | 55 |

(ii) Systemic Effects—ACTH Suppression in Adrenalectomised Rats

Male CD rats (90–120 g) were adrenalectomised under Isoflurane anaesthesia and drinking water was supplemented with 0.9% saline. Four days later the animals receive a single intra-tracheal dose (under Isoflurane anaesthesia) of compound suspended in saline (containing 0.2% Tween-80, 0.2 ml) at 10am. After 4 h animals are sacrificed by administration of Euthetal and blood samples are taken by intracardiac puncture and collected into heparinised tubes. The samples are centrifuged (20 minutes at 1000 RPM at 4 deg C.), the plasma is collected and assayed by Radioimmunoassay (RIA) for Adrenocorticotrophic hormone (ACTH) using a DPC double antibody RIA kit. Intact and vehicle control groups were included in each experiment in order to account for diurnal variation in ACTH and effects of vehicle. Results are calculated with respect to the RIA standard curve and expressed as ACTH pg/ml plasma, allowing percentage reduction in ACTH to be calculated.

| Compound | Dose | % Reduction in ACTH |
|---|---|---|
| Fluocinolone acetonide | 1 µg | 49 |
| Fluocinolone acetonide | 5 µg | 84 |
| Example 2 Isomer A | 125 µg | 5 |
| Example 2 Isomer A | 250 µg | 29 |
| Example 2 Isomer A | 500 µg | 45 |

This result illustrates the minimal systemic effects associated with these plasma labile derivatives Pharmaceutical Formulations The following are examples of suitable formulations of compounds of the invention. The term "active ingredient" is used herein to represent a compound of the invention and can be, for example, the isomers (or a mixture thereof) of Example 3.

1. Inhalation Cartridges

| Active ingredient micronised | 1.6% w/w |
|---|---|
| Lactose BP | 98.4% w/w. |

The active ingredient is micronised in a conventional manner to a fine particle size range such as to permit inhalation of substantially all of the medicament into the lungs upon administration, prior to blending with normal tableting grade lactose in a high energy mixer. The powder blend is filled into gelatin capsules on a suitable encapsulating machine. The contents of the cartridges are administered using a powder inhaler such as ROTAHALER™ inhaler. Alternatively, the powder blend can be filled into blisters of a blister pack or strip. The contents of the blister pack or strip are administered using a powder inhaler such as DISKHALER™ or DISKUS™ inhaler. [ROTAHALER, DISKHALER and DISKUS are trade marks of the Glaxo Wellcome group of companies].

2. Aerosol Formulation

(i) Suspension

|  | mg/actuation | per can |
|---|---|---|
| Active ingredient micronised | 0.25 | 40 mg |
| 1,1,1,2-tetrafluoroethane | 74.75 | 11.96 g |

The active ingredient is weighed directly into an open aluminium can and a metering valve is then crimped in place. 1,1,1,2-Tetrafluoroethane is then added to the can under pressure through the valve and the can shaken to disperse the drug. The resultant inhaler contains 0.33% w/w active ingredient.

(ii) Solution

|  | mg/actuation | per can |
|---|---|---|
| Active ingredient micronised | 0.25 | 40 mg |
| Ethanol (anhydrous) | 7.5 | 1.2 g |
| 1,1,1,2-tetrafluoroethane | 67.25 | 10.76 g |

Active ingredient is dissolved in the ethanol. The resultant ethanolic solution of active ingredient is metered into an open aluminium can and a metering valve is then crimped in place 1,1,1,2-Tetrafluoroethane is then added under pressure through the valve. The resultant inhaler contains 0.33% w/w active ingredient and 10% w/w ethanol.

3. Cream

|  | % w/w |
|---|---|
| Active ingredient micronised | 0.2 |
| Liquid Paraffin | 40 |
| Cetostearyl alcohol | 5 |
| Cetomacrogol 1000 | 1 |
| Isopropylmyristate | 5 |
| Propylene glycol | 10 |
| Benzoic acid | 0.2 |
| Sodium phosphate | 0.05 |
| Citric acid/monohydrate | 0.05 |
| Purified water to | 100 |

The micronised active ingredient is dispersed in a portion of the water containing a portion of the cetomacrogol 1000. The liquid paraffin, cetostearyl alcohol and isopropyl myristate are melted together, cooled to 50 to 60° C. and added to the remaining water containing the propylene glycol, benzoic acid (preservative), and sodium phosphate and citric acid (buffering agents). The resultant oil phase is added to the active ingredient suspension with stirring until cool.

Protection may be sought for any subject matter described herein. Thus, protection may be sought for the compounds (including intermediates), compositions, processes and uses described herein.

What is claimed is:

1. A compound of formula (I)

and solvates thereof in which
$R_1$ and $R_2$ are the same or different and each represents hydrogen or $C_{1-6}$ alkyl;
$R_3$ and $R_4$ are the same or different and each represents hydrogen or halogen; and

----- represents a single or a double bond.

2. A compound according to claim 1 in which $R_1$ and $R_2$ are the same or different and each represents hydrogen or $C_{1-3}$ alkyl.

3. A compound according to claim 1 in which $R_1$ and $R_2$ are the same or different and each represents hydrogen, methyl or n-propyl.

4. A compound according to claim 1 in which $R_1$ and $R_2$ are both methyl.

5. A compound according to claim 1 in which $R_1$ and $R_2$ are different and each represents hydrogen or n-propyl.

6. A compound according to claim 1 in which $R_3$ and $R_4$ are the same or different and each represents hydrogen, fluorine or chlorine.

7. A compound according to claim 1 in which $R_3$ and $R_4$ are the same or different and each represents hydrogen or fluorine.

8. A compound according to claim 1 in which $R_3$ and $R_4$ are both fluorine.

9. A compound according to claim 1 in which S is bonded to the alpha carbon atom of the lactone moiety.

10. 6α,9α-Difluoro-11β-hydroxy-16α,17α-isopropylidenedioxy-17β-(2-oxo-tetrahydro-furan-3-yl-sulfanyl)-androst-4-en-3-one;
   6α,9α-Difluoro-11β-hydroxy-16α,17α-isopropylidenedioxy-17β-(2-oxo-tetrahydro-furan-3-yl-sulfanyl)-androsta-1,4-dien-3-one;
   16α,17α-(R-Butylidenedioxy)-6α,9α-difluoro-11β-hydroxy-17β-(2-oxo-tetrahydro-furan-3-yl-sulfanyl)-androsta-1,4-dien-3-one;
   16α,17α-(R-Butylidenedioxy)-6α,9α-difluoro-11β-hydroxy-17β-(2-oxo-tetrahydro-furan4-yl-sulfanyl)-androst-4-en-3-one;
   16α,17α-(R-Butylidenedioxy)-6α,9α-difluoro-11β-hydroxy-17β-(2-oxo-tetrahydro-furan-3-yl-sulfanyl)-androst-4-en-3-one;
and solvates thereof.

11. A pharmaceutical composition comprising a compound of formula (I) as defined in claim 1 or a physiologically acceptable solvate thereof, together, if desirable, in admixture with one or more physiologically acceptable diluents or carriers.

12. A method for the treatment of a human or animal subject with an anti-inflammatory and/or allergic condition, which method comprises administering to said human or animal subject an effective amount of a compound of formula (I) as defined in claim 1 or a physiologically acceptable solvate thereof.

13. A process for preparing a compound of formula (I) according to claim 1, the process comprising A) treating a compound of formula (II)

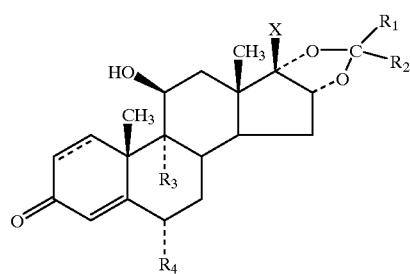

(II)

in which $R_1$, $R_2$, $R_3$, $R_4$ and

----- are as defined in claim 1 and X is a thiohydroxamate ester group, with a compound of formula (III)

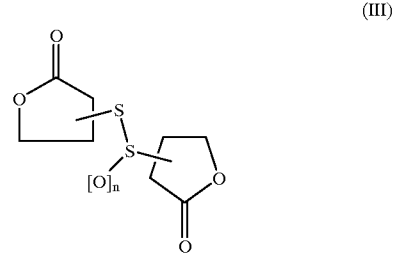

(III)

in which n is 0 or 2;

B) converting of a compound of formula (I) to a transacetylated or hydrogenated compound of formula (I); or C) deprotecting a hydroxyl protected derivative of a compound of formula (I);

followed if necessary by (i) solvate formation or (ii) preparation of an individual isomer of a compound of formula (I).

* * * * *